May 21, 1957 W. KORDES Plant Pat. 1,604
ROSE PLANT
Filed Sept. 21, 1956
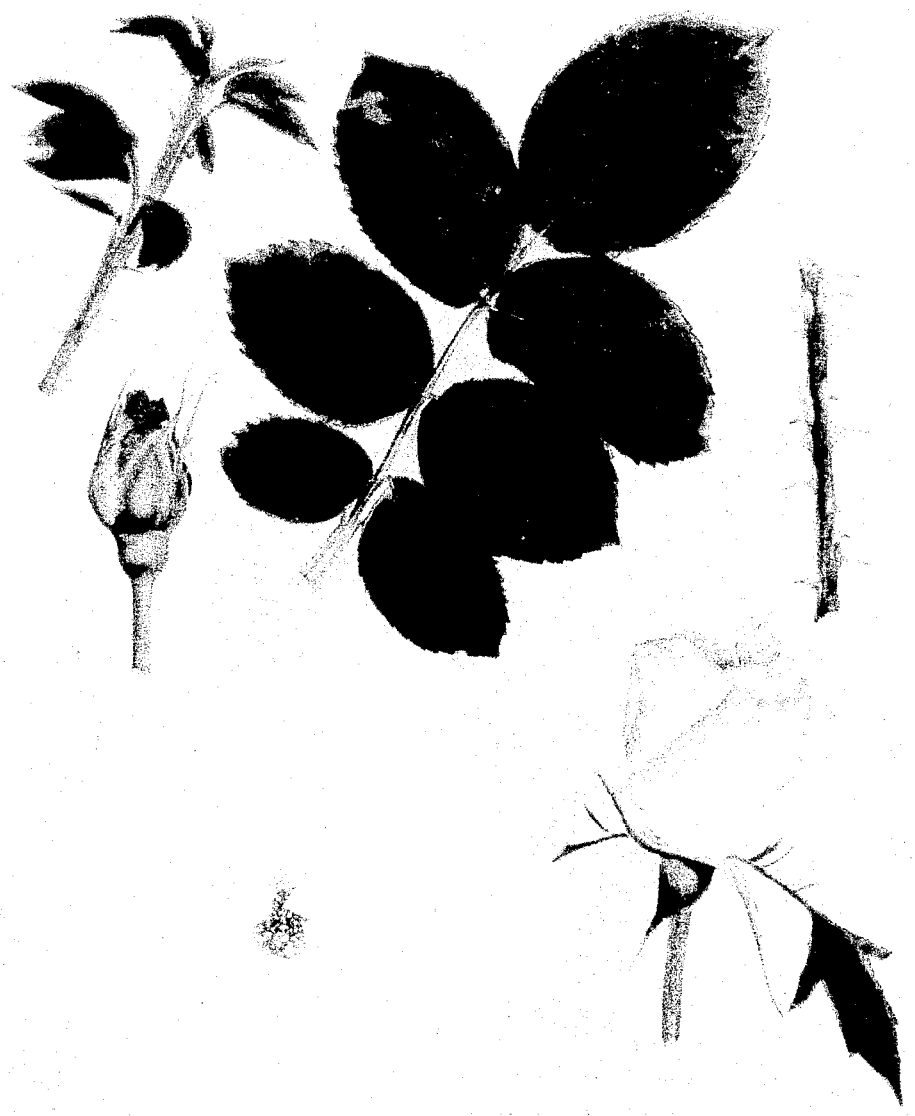
Inventor.
Wilhelm Kordes
By: Robb & Robb
Attorneys.

United States Patent Office

Plant Pat. 1,604

Patented May 21, 1957

1,604

ROSE PLANT

Wilhelm Kordes, near Elmshorn in Holstein, Sparrieshoop, Germany, assignor to Jackson & Perkins Company, Newark, N. Y., a corporation of New York Application September 21, 1956, Serial No. 611,399

1 Claim. (Cl. 47—61)

The present invention relates to a new and distinct variety of rose plant of the hybrid tea class, which was originated by me by crossing the variety "Golden Scepter" (Plant Patent No. 910) with the variety "Karl Herbst" (unpatented).

The primary objective of this breeding was to produce a new rose variety which combines some of the openness and vigor of "Golden Scepter" with the characteristics of "Karl Herbst," the latter parent having originated from a cross of "Independence" (Plant Patent No. 1036) and "Peace" (Plant Patent No. 591), thereby further combining in the new variety some of the characteristics of "Peace." This objective was fully attained, as evidenced by the following characteristics which are outstanding in the new variety:

(1) The healthy and vigorous habits of plant growth;
(2) Its leathery and glossy dark Cress Green foliage;
(3) Its large flowers;
(4) The distinctive Marguerite Yellow general color tonality of the center of the flower, with the edges of the petals of Deep Rose Pink and suffusing the color of the flower center; and
(5) A corresponding bud color showing deeper colored edges with a suffusion of color in the center.

Considered altogether, the foregoing characteristics and distinctions definitely differentiate my new variety from its parents, as well as from all others of its class of which I am aware, and represent a unique combination in a hybrid tea rose variety.

Asexual reproduction of the new variety by budding, as performed at Newark, New York, U. S. A., and also at Pleasanton, California, U. S. A., shows that the foregoing characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of the new variety, with color terminology in accordance with Ridgeway's Color Standards and Nomenclature:

Parentage: Seedling.
*Seed parent.*—"Golden Scepter."
*Pollen parent.*—"Karl Herbst."
Classification:
*Botanic.*—Hybrid tea.
*Commercial.*—Hybrid tea.

*Flower*

(Observations made from specimens grown outdoors at Newark, New York, U. S. A., in the early afternoon near the middle of August.)

Blooming Habit: Recurrent—continuous.
Bud:
*Size.*—Large.

*Form.*—Urn; is not affected by wet or hot weather.
*Color.*—When sepals first divide—Dahlia Carmine, Plate 26. When petals begin to unfurl—Marguerite Yellow, Plate 30, in center of petal, with outer edge of petal Tyrian Rose, Plate 12. When half-blown: inside of petals—Marguerite Yellow, Plate 30, in the center of petal, with lower half of petal lightly overcast with Buff Yellow, Plate 4, and with outer edge of petal Spinel Pink, Plate 26, lightly overcast with Spinel Red, Plate 26. Reverse of petals—Marguerite Yellow, Plate 30, with lower half of petal lightly overcast with Buff Yellow, Plate 4, and with outer edge of petal lightly overcast with Rose, Plate 12.
*Sepals.*—Branched; curl back when petals begin to unfurl. Color: inside—Light Cress Green, Plate 31; outside—Biscay Green, Plate 17.
*Calyx.*—Color—Bice Green, Plate 17. Shape—funnel. Size—broad. Aspect—smooth. Odor when rubbed—none.
*Peduncle.* — Length — medium. Aspect — rough. Strength—erect; slender. Color—Biscay Green, Plate 17.
*Opening.*—Opens up wall; is not affected by adverse weather conditions.

Bloom:
*Size.*—Large. Average size when fully expanded—from 4½ to 5 inches.
*Borne.*—Both singly and several together.
*Stems.*—Medium length; strong.
*Form (when first open).*—High center. Permanence—retains its form to the end, but outer petals curl back.
*Petalage.*—Double (full but open center). Number of petals under normal conditions—from 65 to 70.
*Color.*—Center of flower—Deep Chrome, Plate 3, with edges of petal Thulite Pink, Plate 27. Outer petals—lower half of petal Marguerite Yellow, Plate 30, with outer edge of petal Spinel Pink, Plate 26, lightly overcast with Deep Rose Pink, Plate 12. Base of petals (aiglet)—Lemon Chrome, Plate 4. Inside of Petals—Marguerite Yellow, Plate 30, at center, with edge of petal Deep Rose Pink, Plate 26. Reverse of petals—Marguerite Yellow, Plate 30, with lower half of petal lightly overcast with Barium Yellow, Plate 16, and with outer edge of petal Thulite Pink, Plate 26. General tonality from a distance—Marguerite Yellow, Plate 30, at center, with edges of petals Deep Rose Pink, Plate 12.
*Discoloration.*—General tonality at end of first day—Marguerite Yellow, Plate 30, at center, with edges of petal Deep Rose Pink, Plate 12, lightly overcast with Spinel Pink, Plate 26. Second day—Marguerite Yellow, Plate 30, lightly overcast with Deep Rose Pink, Plate 12, which in turn is lightly overcast with Spinel Pink, Plate 26. Third day—Marguerite Yellow, Plate 30, lightly overcast with Spinel Pink, Plate 26.

Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Strong. Nature—tea (average hybrid tea scent).

*Lasting quality.*—On the plant—long. As cut flower—very long.

*Genital organs*

Stamens, anthers: Medium size; many; regularly arranged around styles. Color—Ochraceous Orange, Plate 15,
Stamens, filaments (threads): Medium length. Color—Pale Lemon Yellow, Plate 4.
Pollen: Color—Baryta Yellow, Plate 4.
Styles: Bunched; uneven length; medium length; thin.
Stigmas: Color—Orange Buff, Plate 3.
Ovaries: All enclosed in calyx.
Hips: None.
Seeds: None.
Form: Bush.
Growth: Vigorous; upright.
Foliage: Compound of 3, 5 or 7 leaflets.
*Size.*—Large.
*Quantity.*—Normal.
*Color.*—Old foliage: upper side—Dark Cress Green, Plate 31; under side—Light Cress Green, Plate 31. New foliage: upper side—Indian Lake, Plate 26; under side—Deep Dull Yellow Green, Plate 32, lightly overcast with Spinel Red, Plate 26.
*Shape.*—Oval.
*Texture.*—Upper side—leathery; glossy. Under side—smooth.
*Ribs and veins.*—Ordinary.
*Edge.*—Serrated (saw-toothed).
*Serration.*—Both double and single; sharp.
*Leaf stem.*—Color—Rainette Green, Plate 31. Under side—smooth.
*Stipules.*—Medium length; slightly bearded.

Wood:
*New wood.*—Color—Lettuce Green, Plate 5. Bark—smooth.
*Old wood.*—Color—Cress Green, Plate 31. Bark—smooth.
Thorns:
*Thorns.*—Quantity: on main stalks from base—many; on laterals from stalk—many. Form—narrow base; medium length; some hooked downward and some hooked upward. Color (when young)—Spinel Red, Plate 26. Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by its healthy and vigorous habits of growth, its leathery and glossy Dark Cress Green foliage, its large flowers, the distinctive Marguerite Yellow general color tonality at the center of the flower with the edges of the flower petals of Deep Rose Pink and suffusing the color in the center, and the corresponding color of its buds which show deep colored edges and suffusing the color in the center thereof.

No references cited.